United States Patent [19]

Charlton et al.

[11] Patent Number: 5,856,195
[45] Date of Patent: Jan. 5, 1999

[54] METHOD AND APPARATUS FOR CALIBRATING A SENSOR ELEMENT

[75] Inventors: Steven C. Charlton, Osceola; Larry D. Johnson, Mill Creek; Matthew K. Musho, Granger; Joseph E. Perry, Osceola, all of Ind.

[73] Assignee: Bayer Corporation, Elkhart, Ind.

[21] Appl. No.: 740,564

[22] Filed: Oct. 30, 1996

[51] Int. Cl.⁶ .......................... G01N 33/48; G01N 33/50; G01N 35/00; G01N 21/00
[52] U.S. Cl. .................... 436/50; 436/8; 436/14; 436/43; 436/44; 436/46; 436/48; 436/164; 436/165; 364/497; 364/571.01; 204/403
[58] Field of Search ..................... 436/8, 50, 14, 436/43–44, 46, 48, 164, 165; 422/64, 58, 67; 364/497, 500, 571.01; 204/403, 406, 407

[56] References Cited

U.S. PATENT DOCUMENTS

| | | | |
|---|---|---|---|
| 5,597,532 | 1/1997 | Connolly | 422/58 |
| 5,628,890 | 5/1997 | Carter et al. | 204/403 |
| 5,630,986 | 5/1997 | Charlton et al. | 422/64 |
| 5,700,695 | 12/1997 | Yassinzadeh et al. | 436/180 |

*Primary Examiner*—Lila Feisee
*Assistant Examiner*—Michael Pak
*Attorney, Agent, or Firm*—Jerome L. Jeffers

[57] ABSTRACT

A method and apparatus are provided for calibrating a sensor for determination of analyte concentration. The meter includes a sensor for receiving a user sample to be measured and a processor for performing a predefined test sequence for measuring a predefined parameter value. A memory can be coupled to the processor for storing predefined parameter data values. A calibration code is associated with the sensor and read by the processor before the user sample to be measured is received. The calibration code is used in measuring the predefined parameter data value to compensate for different sensor characteristics.

21 Claims, 12 Drawing Sheets

| CONTACT | SET 70A |
|---|---|
| | SYNC |
| A | |
| B | OUTER |
| C | INNER OR OUTER |
| D | INNER OR OUTER |
| E | INNER OR OUTER |
| F | INNER OR OUTER |
| G | INNER OR OUTER |
| H | INNER OR OUTER |
| I | INNER OR OUTER |
| J | INNER OR OUTER |

70B

| CONTACT | TYPE 1 | TYPE 2 | TYPE 3 | TYPE 4 |
|---|---|---|---|---|
| A | SYNC 1 | SYNC 1 | SYNC 1 | SYNC 1 |
| B | INNER OR OUTER | INNER OR OUTER | INNER OR OUTER | INNER OR OUTER |
| C | SYNC 2 | SYNC 2 | INNER OR OUTER | INNER OR OUTER |
| D | INNER OR OUTER | INNER OR OUTER | SYNC 2 | INNER OR OUTER |
| E | INNER OR OUTER | INNER OR OUTER | INNER OR OUTER | SYNC 2 |
| F | INNER OR OUTER | INNER OR OUTER | INNER OR OUTER | INNER OR OUTER |
| G | INNER OR OUTER | INNER OR OUTER | INNER OR OUTER | INNER OR OUTER |
| H | INNER OR OUTER | INNER OR OUTER | INNER OR OUTER | INNER OR OUTER |
| I | INNER OR OUTER | OUTER | OUTER | INNER OR OUTER |
| J | OUTER | | | OUTER |

FIG.6D

| NUMER OF RESISTANCES VALUES | NUMBER OF DISTINCT CALIBRATION CODES |
|---|---|
| 2 | 3 |
| 3 | 6 |
| 4 | 10 |
| 5 | 15 |
| 6 | 21 |
| * | * |
FIG.7D
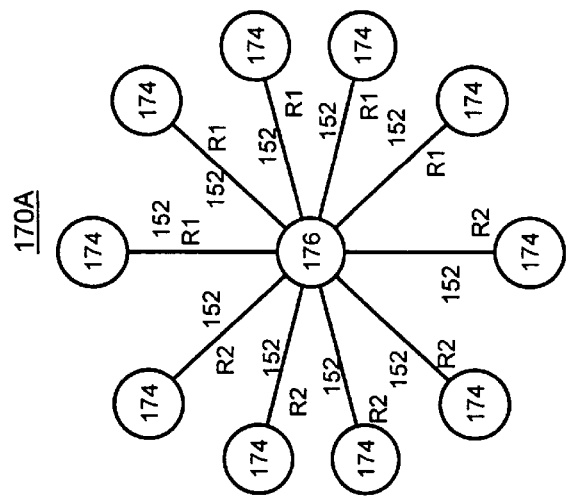
FIG.7C
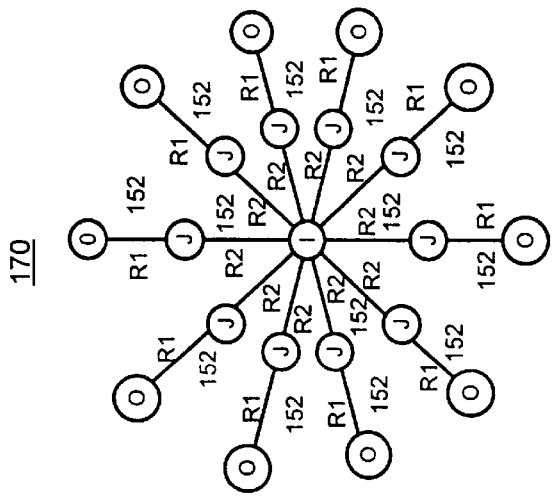
FIG.7B

METHOD AND APPARATUS FOR CALIBRATING A SENSOR ELEMENT

FIELD OF THE INVENTION

The present invention generally relates to a sensor, and, more particularly, to a new and improved method and apparatus for calibrating a sensor element.

DESCRIPTION OF THE PRIOR ART

The field of clinical chemistry is concerned with the detection and quantitation of various substances in body material, typically body fluids such as blood, urine or saliva. In one important aspect of this field, the concentration of naturally occurring substances, such as cholesterol or glucose, in an individual's blood is determined. One of the most frequently used analytical devices in clinical chemistry for determining the concentration of an analyte in a fluid sample is the test sensor. Upon contacting the test sensor with the fluid sample, certain reagents incorporated into the sensor react with the analyte whose concentration is being sought to provide a detectable signal. The signal may be a change in color as in the case of a colorimetric sensor or a change in current or potential as in the case of an electrochemical system. For a particular class of electrochemical sensors, i.e. amperometric sensors, the detected current is proportional to the concentration of the analyte in the fluid sample being tested. Those systems which employ an enzyme in the reagent system may be referred to as biosensors since they rely on the interaction of the enzyme (a biological material) with the analyte to provide the detachable response. This response, whether it be a change in color or in current or in potential, is typically measured by a meter, into which the sensor is inserted, which meter provides a readout of the analyte concentration such as by means of a LCD system.

In particular, the determination of glucose in blood is of great importance to diabetic individuals who must frequently check the level of glucose in connection with regulating the glucose intake in their diets and their medications. While the remainder of the disclosure herein will be directed towards the determination of glucose in blood, it is to be understood that the procedure and apparatus of this invention can be used for the determination of other analytes in other body fluids or even non-fluid body materials such as the detection of occult blood in fecal material upon selection of the appropriate enzyme. In addition such sensors can be used in, for example, testing for meat spoilage or foreign substances in well water.

Diagnostic systems, such as blood glucose measuring systems, typically calculate the actual glucose value based on a measured output and the known reactivity of the reagent sensing element used to perform the test. The latter information can be given to the user in several forms including a number or character that they enter into the instrument, a sensed element that is similar to a test sensor but which is capable of being recognized as a calibration element and its information read by the instrument or a memory element that is plugged into the instrument's microprocessor board and is read directly.

Various arrangements have been used to provide lot calibration information into the instrument. The base method requires the user to enter a code number which the instrument can use to retrieve calibration constants from a lookup table. U.S. Pat. No. 5,266,179 discloses a resistor whose resistance value can be measured by the instrument. From the resistance value the calibration constants are recovered.

The Advantage system and Accucheck series of glucose meters marketed by Boehringer Mannheim Diagnostics employ a reagent calibration method based on an integrated circuit (IC) chip. This chip is included in each reagent package purchased by the customer. Information about how the instrument is to calibrate itself for that particular lot of reagent is contained on the IC. The customer must attach the IC to the instrument by slipping the IC into a connection port located on the instrument. The IC may be interrogated for its information each time the user turns on the instrument. All these systems require the user to interact directly for calibration information to be available to the instrument and therefore, for a successful glucose number to be calculated.

SUMMARY OF THE INVENTION

Important objects of the present invention are to provide a new and improved method and apparatus for calibrating a sensor and to provide such method and apparatus that eliminates or minimizes the need for user interaction.

In brief, a method and apparatus are provided for calibrating a sensor element. The sensor element is used in a sensor system which includes a sensor meter, a sensor element for receiving a user sample to be analyzed and a processor for performing a predefined test sequence for measuring a predefined parameter value. A memory is coupled to the processor for storing predefined parameter data values. An autocalibration code is associated with the sensor and read by the processor before the user sample to be measured is received. The autocalibration code is used in measuring the predefined parameter data value to compensate for different characteristics of sensors which will vary on a batch to batch basis.

BRIEF DESCRIPTION OF THE DRAWINGS

The present invention together with the above and other objects and advantages may best be understood from the following detailed description of the preferred embodiments of the invention illustrated in the drawings, wherein:

FIG. 6D is a chart illustrating further alternative digital autocalibration encoding labels in accordance with the present invention of the sensor meter of FIG. 1;

FIG. 7B expanded views of alternative analog autocalibration encoding labels useful in the present invention;

FIG. 7C expanded views of alternative analog autocalibration encoding labels useful in the present invention;

FIG. 7D is a chart illustrating further alternative analog autocalibration encoding labels in accordance with the present invention of the sensor meter of FIG. 1;

DETAILED DESCRIPTION OF THE PREFERRED EMBODIMENTS

Figure 1:
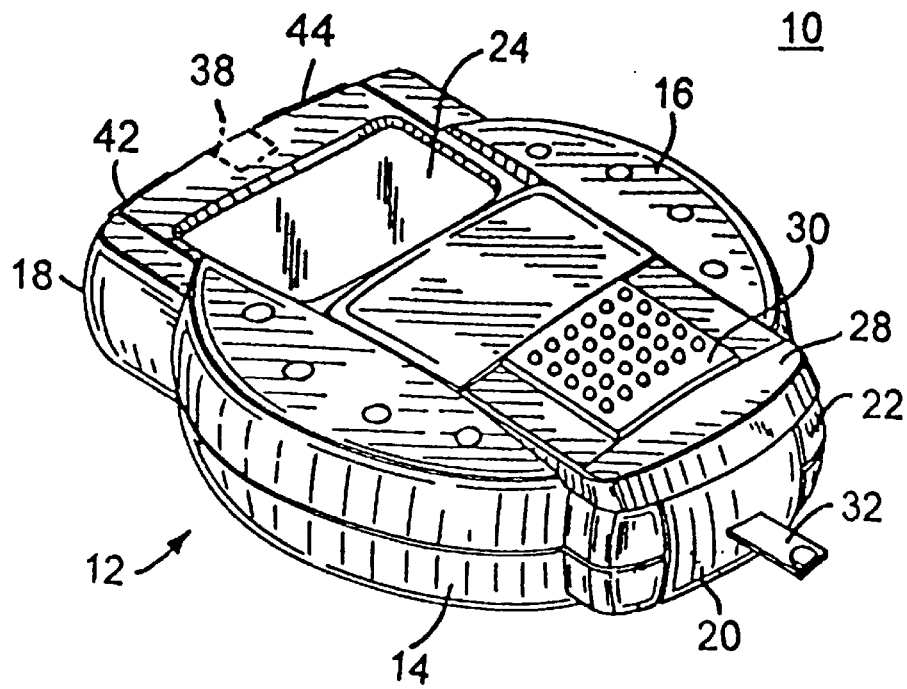
FIG. 1 is an enlarged perspective view of a sensor meter shown with the slide in an open position in accordance with the present invention.
Figure 2:
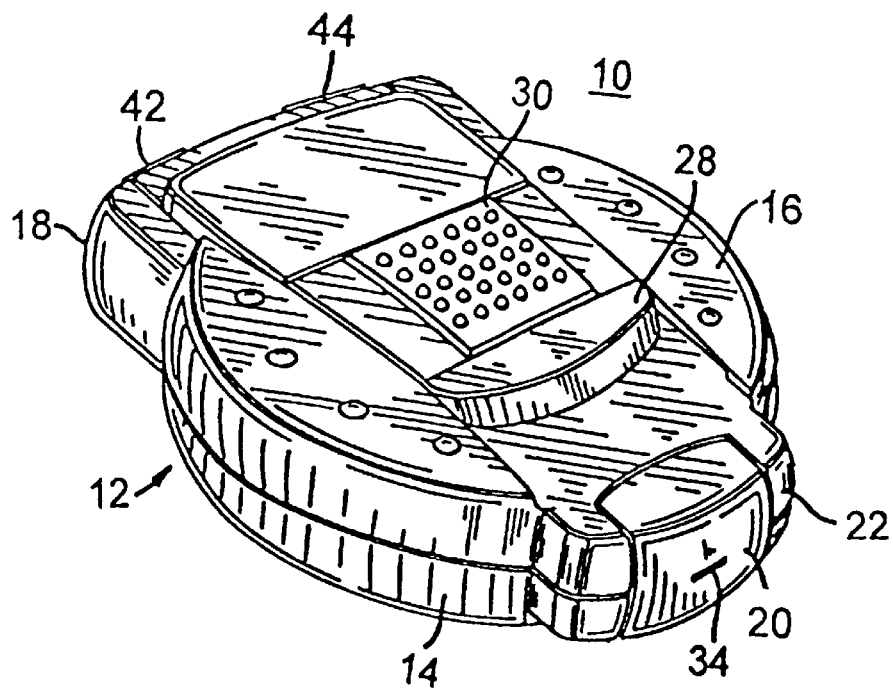
FIG. 2 is an enlarged perspective view of the sensor meter of FIG. 1 with the slide in a closed position.
Figure 3:
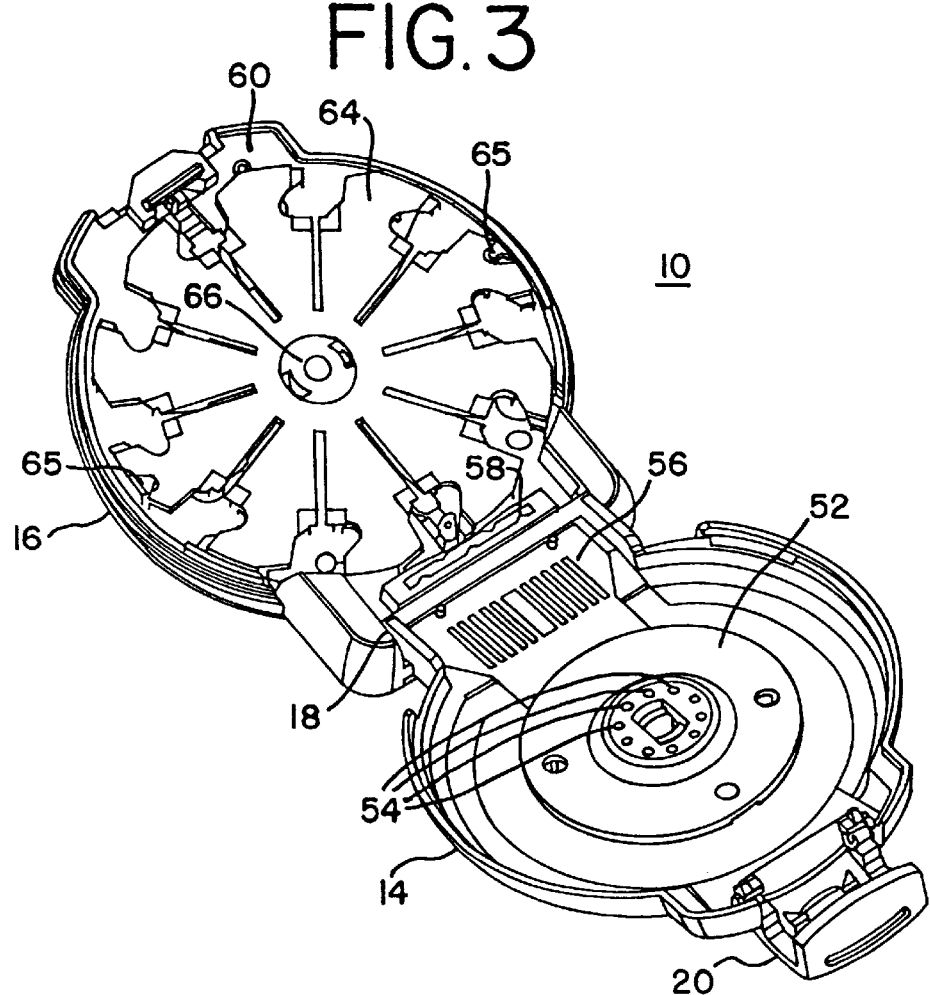
FIG. 3 is an enlarged perspective view of the sensor meter of FIG. 1 illustrating an interior thereof.

Making reference now to the drawings, in FIGS. 1, 2 and 3 there is illustrated a sensor meter designated as a whole by the reference character 10 and arranged in accordance with principles of the present invention. Sensor meter 10 includes a clam-shell type housing enclosure 12 formed by a base member 14 and a cover member 16. Base and cover members 14 and 16 are pivotably attached together at a first end 18 and are secured together by a latch member 20 at a second, opposite end 22. A display 24, such as a liquid crystal display (LCD) is carried by the cover member 16. To turn the sensor meter 10 on and off, a manually movable slide 28 mounted on the cover member 16 is moved between an open position shown in FIG. 1 and a closed position shown in FIG. 2.

In the closed or OFF position of FIG. 2, the slide 28 covers the display 24. A thumb grip 30 carried by the slide 28 is arranged for manual engagement by a user of the sensor meter 10 to select the ON and OFF positions. The thumb grip 30 also is movable from left to right in the OFF position of slide 28 for selecting a system test operational mode. When a user moves the slide 28 to the ON position of FIG. 1, the display is uncovered and a sensor 32 is presented. The sensor 32 extends through a slot 34 and is positioned outside the enclosure 12 for the user to apply a blood drop. A right button 42 and a left button or switch 44 (or switches A and B in FIG. 7) are carried by the enclosure 12 for operation by a user to select predefined operational modes for the sensor meter 10, and for example, to set, recall and delete blood glucose readings and to set date, time, and options.

Figure 4:
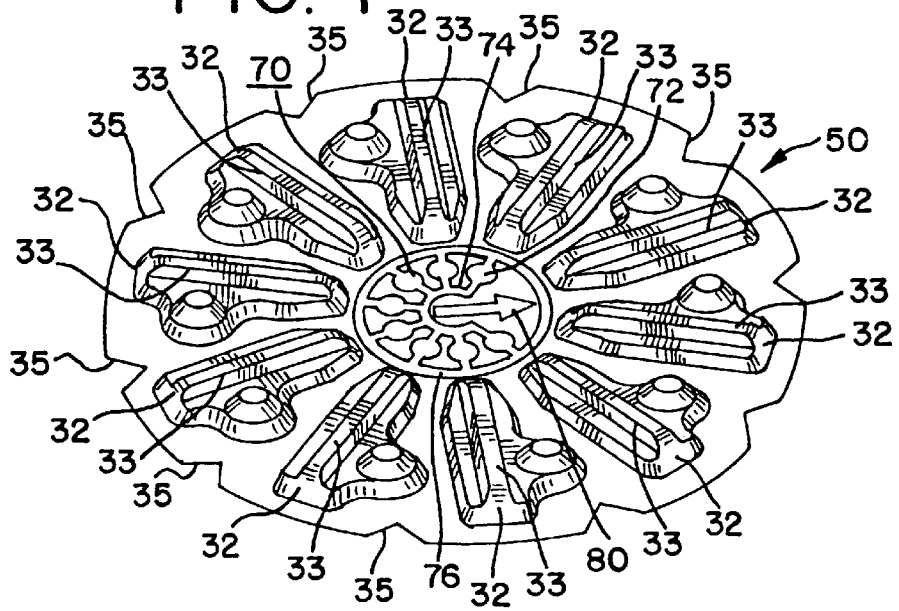
FIG. 4 is an enlarged perspective view of an exemplary sensor package illustrating a preferred arrangement of an autocalibration encoding label attached to a diskette of sensors in accordance with the present invention of the sensor meter of FIG. 1.

Referring now to FIGS. 3 and 4, in FIG. 3, the inside of the sensor meter 10 is shown without a sensor package. An exemplary sensor package generally designated by the reference character 50 is separately illustrated in FIG. 4. Sensor meter base member 14 supports an autocalibration plate 52 and a predetermined number of autocalibration pins 54, for example, ten autocalibration pins 54, as shown. The autocalibration pins 54 are connected via a flex circuit 56 and an autocalibration connector 58 to associated sensor circuitry 81 as illustrated and described with respect to FIG. 5, and FIG. 6A or FIG. 7A. Sensor circuitry 81 is located in the upper part of the sensor meter 10 between the cover 16 and a block guide 60. A disk retainer 66 and an indexing disk 64 are provided within the cover member 16. The indexing disk 64 includes a pair of locking projections 65 for engagement with cooperative triangular shaped recessed portions 35 of the sensor package 50 for receiving and retaining the sensor package 50 on the indexing disk 64. Sensor package 50 carries an autocalibration label generally designated by the reference character 70 (170 in FIG. 7B or 170A in FIG. 7C).

In accordance with the invention, calibration codes assigned for use in the clinical value computations to compensate for manufacturing variations between sensor lots are encoded upon a tag or label generally designated by 70 that is associated with a sensor package 50 of sensors 32, as shown in FIG. 4. The calibration encoded label 70 is inserted into the instrument with the package 50 of multiple sensors 32 which are stored in individual blisters 33 and read by associated sensor electronic circuitry before a sensor 32 is used. Calculation of the correct test values, such as, glucose values from current readings, is based upon solving a single equation. Equation constants based on a calibration code are identified, such as by either using an algorithm to calculate the equation constants or retrieving the equation constants from a lookup table for a particular predefined calibration code read from the calibration encoded label 70. The calibration encoded label 70 can be implemented by digital, mechanical, analog, optical or a combination of these techniques.

Referring to FIG. 4, the sensor package 50 used in a sensor meter 10 for handling of a plurality of fluid sensors 32. The sensor package 50 includes a plurality of sensor cavities or blisters 33 extending toward a peripheral edge of the sensor package 50. Each sensor cavity 33 accommodates one of the plurality of fluid sensors 32. The sensor package 50 is generally circular in shape with the sensor cavities 33 extending from near the outer peripheral edge toward and spaced apart from the center of the sensor package 50. The sensor package 50 includes an autocalibration data area generally designated by 70 providing autocalibration encoded information. This autocalibration encoded information or autocalibration label 70 includes a plurality of contact pads 72 aligned for electrical contact engagement with the autocalibration pins 54 when the sensor package 50 is received within the sensor meter 10. The autocalibration label 70 includes an inner conductive path or trace 74 and an outer conductive path 76. As described in detail below, selected contact pads 72 are connected to the conductive paths 74 and 76.

Figure 5:
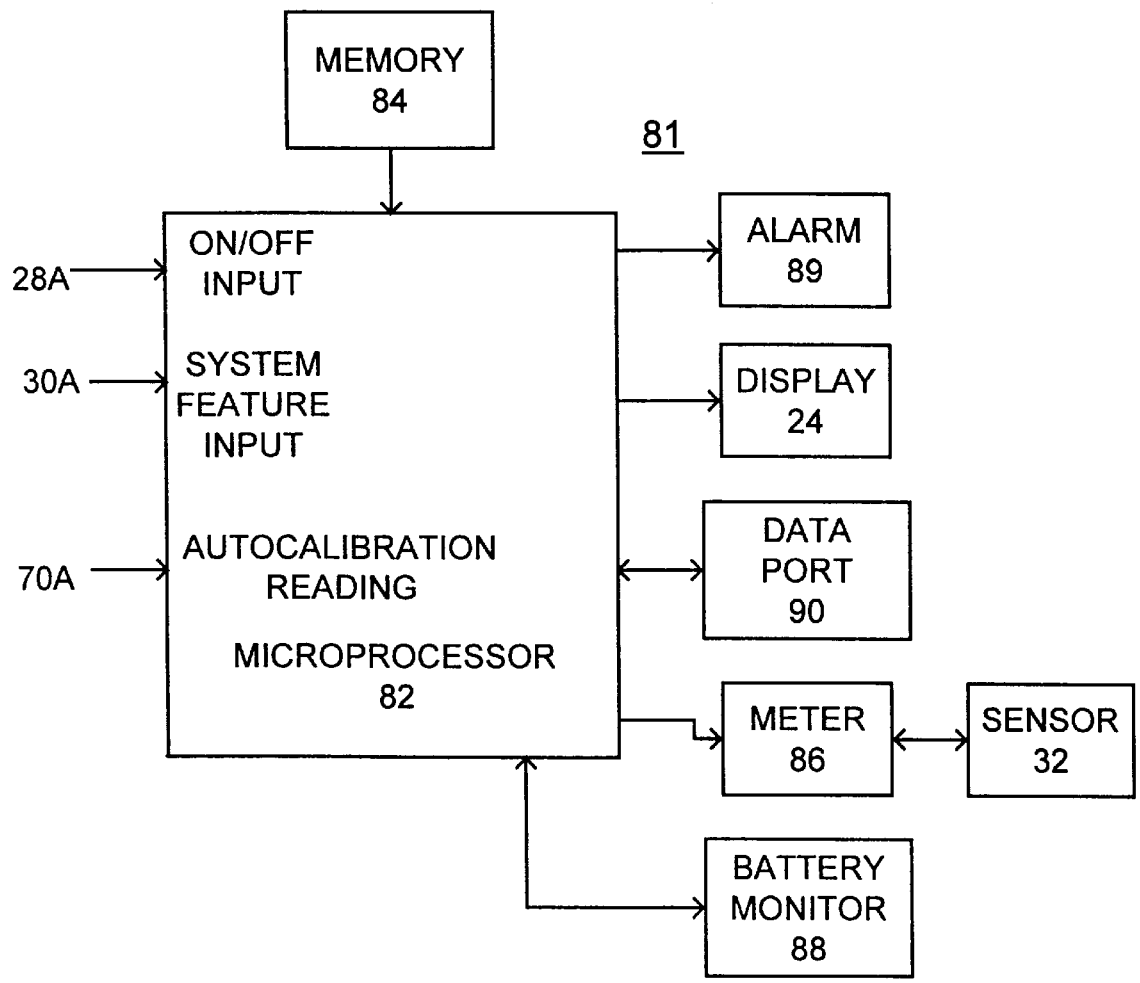
FIG. 5 is a block diagram representation of sensor meter circuitry in accordance with the present invention of the sensor of FIG. 1.

Referring also to FIG. 5, there is shown a block diagram representation of sensor circuitry designated as a whole by the reference character 81 and arranged in accordance with principles of the present invention. Sensor circuitry 81 includes a microprocessor 82 together with an associated memory 84 for storing program and user data. A meter function 86 coupled to sensor 32 is operatively controlled by the microprocessor 82 for recording blood glucose test values. A battery monitor function 88 is coupled to the microprocessor 82 for detecting a low battery (not shown) condition. An alarm function 89 is coupled to the microprocessor 82 for detecting predefined system conditions and for generating alarm indications for the user of sensor meter 10. A data port or communications interface 90 couples data to and from a connected computer (not shown). An ON/OFF input at a line 28A responsive to the user ON/OFF operation of the slide 28 is coupled to the microprocessor 82 for performing the blood test sequence mode of sensor meter 10. A system features input at a line 30A responsive to the user operation of the thumb grip 30 is coupled to the microprocessor 82 for selectively performing the system features mode of sensor meter 10. An autocalibration signal input indicated at a line 70A is coupled to the microprocessor 82 for detecting the autocalibration encoded information for the sensor lot in accordance with the invention. Microprocessor 82 contains suitable programming to perform the methods of the invention as illustrated in FIGS. 8, 9, 10 and 11.

Figure 6A:
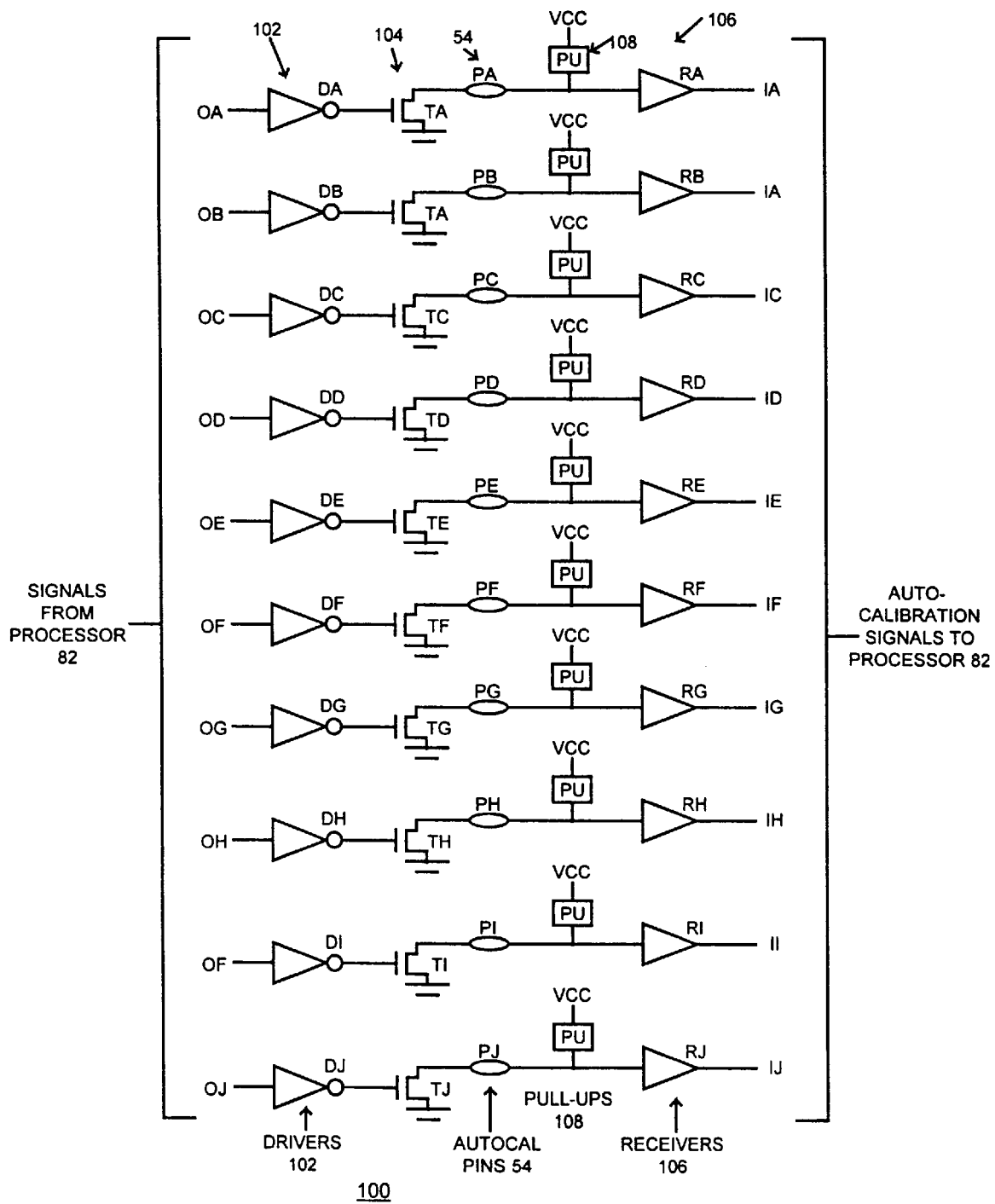
FIG. 6A is a schematic diagram representation of exemplary circuitry for use with a digital autocalibration encoding label of the invention.

FIG. 6A illustrates a digital electronic circuit 100 for a digital calibration method which connects the processor 82 to the label 70. Ten digital output signals from the processor 82 (OA through OJ) connect through ten drivers 102 (DA through DJ) to the ten autocalibration pins 54 (PA through PJ) via the corresponding one of ten p-channel field-effect transistors (FETs) 104 (TA through TJ). The ten autocalibration pins 54 connect to ten receivers 106 (RA through RJ) that provide ten digital input signals (IA through IJ) to the processor 82. Each receiver has an associated pull-up 108 (PU) connected to a supply voltage VCC. The autocalibration pins 54 (PA through PJ) electrically connect to other label contacts 72 on the autocalibration label 70 when the cover 16 is closed and a label 70 is present due to the conductive patterns printed on the particular label 70, for example as shown on labels 70 in FIGS. 4 and 6B.

In operation to read a contact pattern of the label 70, the processor 82 turns on one of the drivers 102, all other drivers 102 are turned off. The enabled driver 102 presents a low signal to the associated autocalibration pin 54. The corresponding receiver 106 for the enabled driver 102 directly connected to the associated autocalibration pin 54 reads as a low signal since this particular driver 102 and receiver 106 are directly connected. All other receivers 106 whose autocalibration pin 54 is also driven low due to the low resistance connection provided by the conductive traces 74, 76, 78 on the label 70 also read as a low signal. All remaining other receivers 102 read as a high signal since the associated driver 104 is not turned-on and the associated pull-up 108 pulls the receiver voltage to VCC.

Figures 6B, 6C:
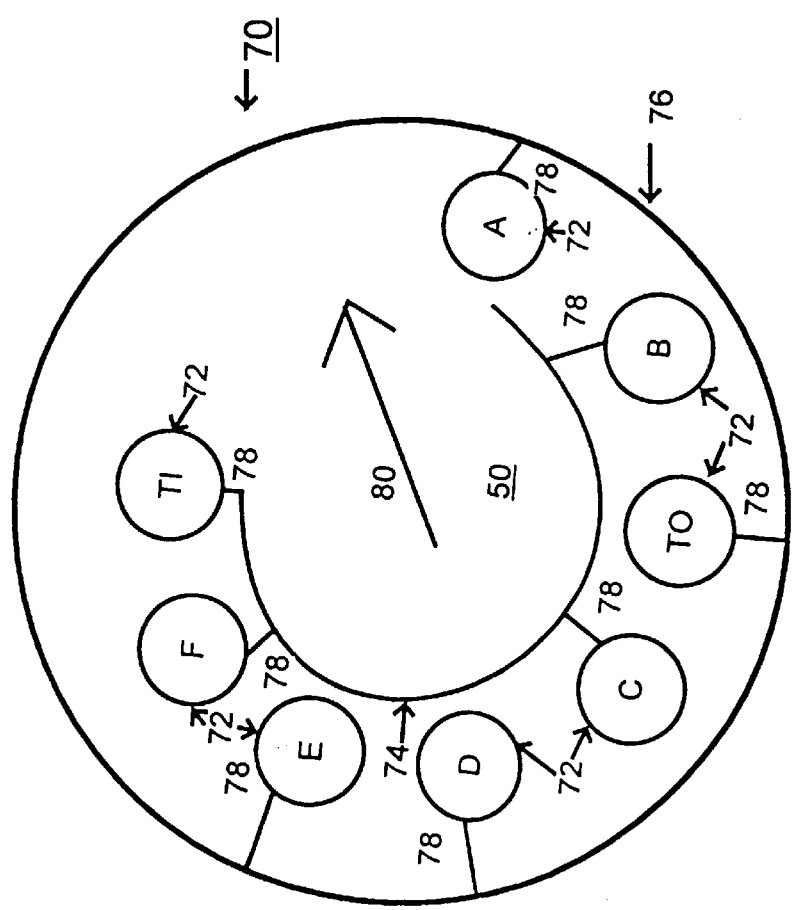
FIG. 6B is an expanded view of a digital autocalibration encoding label useful in the present invention.
FIG. 6C is a chart illustrating an alternative digital autocalibration encoding label in accordance with the present invention of the sensor meter of FIG. 1.

Referring to FIG. 6B, there is shown an enlarged view illustrating a preferred arrangement of the calibration encoded label 70 of the invention. In accordance with a feature of the invention, the calibration encoded label 70 is used to automate the process of information transfer about the lot specific reagent calibration assignment for associated sensors 32. For example, the autocalibration information as illustrated in FIG. 6B can be encoded into the label 70 that is appended to the bottom side of a blister-type package 50 that contains, for example, ten sensors 32 (one in each of 10 individual blisters 33) of a common origin or lot. The calibration encoded label 70 is read at any angular position and deciphered by the sensor meter 10 without any user intervention. The calibration encoded label 70 is read via the plurality of contacts 72 provided at predetermined positions. As shown also in FIG. 4, selected ones of the contacts 72 are connected to an inner ring or path 74, other contacts 72 connected to an outer ring or path 76, and other contacts 72 not connected.

Figure 7A:
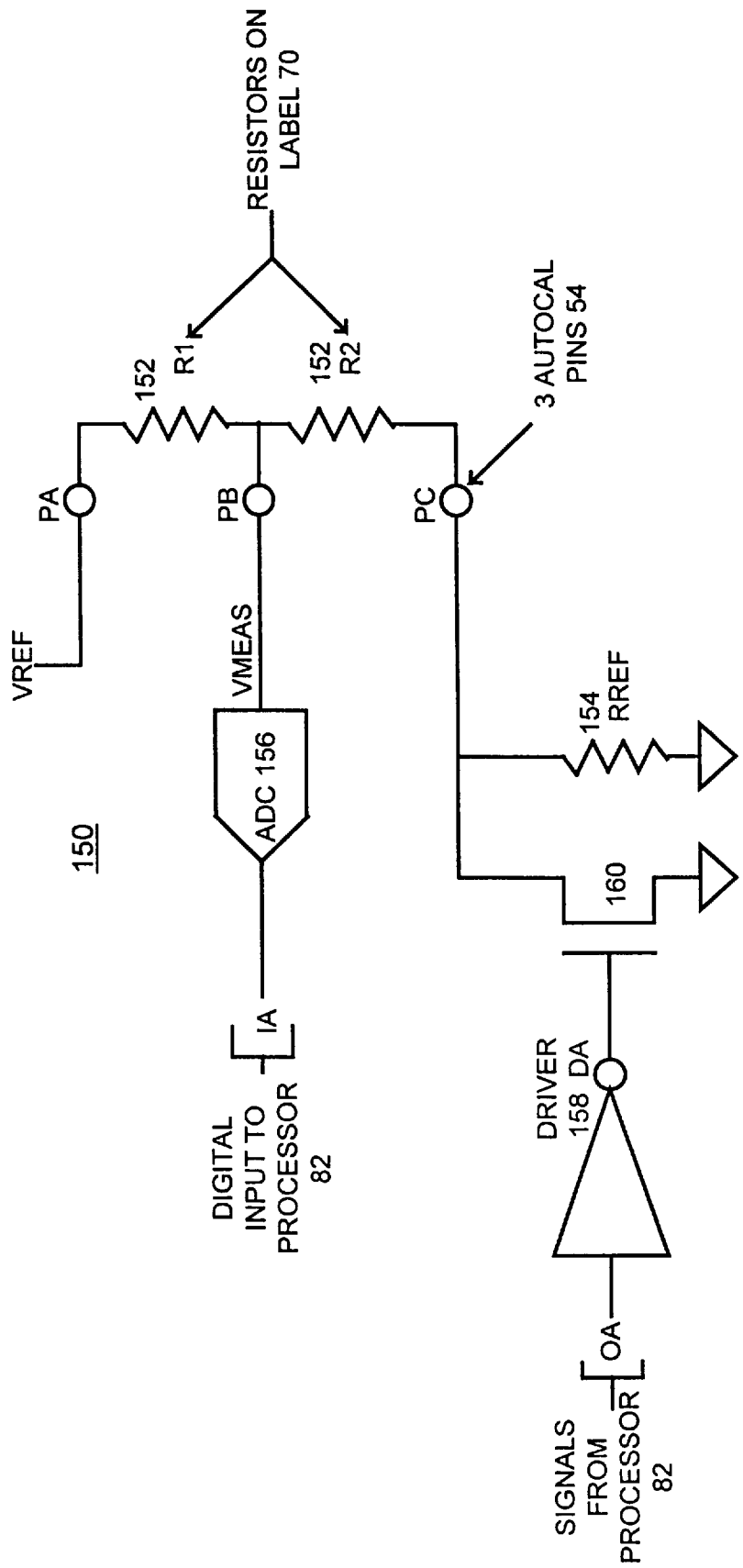
FIG. 7A is a schematic diagram representation of exemplary circuitry for use with an analog autocalibration encoding label of the invention.

A number of both digital and analog arrangements can be employed to define the calibration encoded label of FIGS. 4 and 6B, the calibration encoded label 170 of FIG. 7B, and the calibration encoded label 170A of FIG. 7C. The calibration encoded label 70, 170, and 170A can be constructed by screenprinting conductive ink onto a base substrate, that can either be a separate substrate or the outer sensor package surface 50, as illustrated in FIGS. 4 and 6B. A separate substrate can be attached to the sensor package 50 using an adhesive, either a hot melt, UV-cure or fast-curing adhesive. A conductive ink defining calibration encoded label 70, 170, and 170A preferably is a carbon, silver or a carbon/silver blended ink. The substrate 50 is any print receptive surface including paper, polymer-filled paper or polymer substrate, preferably a heat stabilized polyethyleneteraphthalate (PET) or polycarbonate. Digital calibration encoding can be defined by either direct encoding through printing or cutting traces with a laser, such as a $CO_2$ or Nd:YAG laser, for a particular sensor lot. An analog system as illustrated and described with respect to FIGS. 7A, 7B, 7C and 7D can be used that is based on measuring resistors that are selectively located at predefined positions, for example, represented by lines 152 and connected to the selected contacts O, I, J as shown in FIG. 7B. In the analog label 170 or 170A, resistors at lines 152, or R1 and R2, preferably are of the thick film type applied to the label by standard screen printing technology.

Another feature as shown in FIGS. 4 and 6B of the calibration encoded label 70 is an indicator feature represented by an arrow labeled 80 that replaces one or more non-connected contact 72. Indicator arrow 80 advantageously is used for maintaining a remaining sensor count number displayed to the user of sensor meter 10. Indicator arrow 80 defines a starting or home position of the sensor package 50, so that in those instances when the package of sensors 32 is removed from the instrument 10 and then is re-installed for whatever reason, an accurate remaining sensor count number is enabled. To maintain the remaining sensor count, the sensor package 50 is positioned so that the arrow 80 on the autocalibration label 70 aligns to a predetermined instrument position when the sensor package 50 is inserted in sensor meter 10. The user advances the sensor package 50 (repeatedly if necessary) until a sensor 32 is made available. At this point a sensor counter reflects the proper number of remaining tests.

FIG. 6B illustrates an exemplary trace pattern for calibration encoded label 70. As shown in FIG. 6B, autocalibration label 70 includes three sets of contact connections, first contacts 72, TO, A, D and E connected to the outer ring or path 76 representing a logical 1, second contacts 72, TI, B, C, F connected to the inner ring or path 74 representing a logical 0; and third null contacts or no connection representing the home position or sync. It should be understood that the inner and outer rings 74 and 76 do not have to be complete rings or circles. The label contacts 72 and the traces that form the inner and outer rings 74, 76 are made of an electrically conductive material. The position of the contacts 72 are aligned with autocalibration pins 54 (shown in FIG. 3) in the sensor meter 10 to make electrical contact. Although the calibration encoded label 70 can be positioned in any one of multiple, for example, ten rotary positions as the sensor package 50 is rotated, the label contacts 72 will always be in alignment with pins 54 in the sensor meter 10 when the calibration encoded label 70 is read.

The text which identifies the contacts does not actually appear on the calibration encoded label 70. The arrow 80 is a visual aid to help the user orientate the package 50 containing the label 70 in the instrument. The arrow 80 need not be electrically conductive. The two sync contacts 72 are not actually present on the label, since they are not connected to any other of the multiple contacts 72. A variation of label 70 could include electrically connecting the sync contacts 72 together. The positions of the sync contacts 72 would be on either side of the arrow 80 in FIG. 6B. The contact labeled TI (Tied Inner) always connects to the inner ring 74, and the contact labeled TO (Tied Outer) always connects to the outer ring 76. The contacts labeled A through F connect to both rings in an unprogrammed label. A cut is made in the printed conductive label material to disconnect the contact from the inner or outer ring 74 or 76 in order to program the calibration code into the label 70. Each one of the contacts A through F could be connected to either ring, this represents $2^6=64$ possible combinations. Code 0 (A through F all connected to inner ring) and code 63 (A through F all connected to outer ring) are not permitted, so 62 codes can be programmed with calibration encoded label 70. In order to determine which contacts 72 are the sync contacts, and which contacts 72 are connected to the inner and outer rings 74 and 76, one contact 72 at a time is set as a low output (zero). Any contacts 72 that are on the same ring 74 or 76 as the low contact will also register low due to the electrical connection provided by the conductive traces on the label 70. Because the sync contacts are not connected to either ring 74 or 76, they register as the only low contact when either is set low. This means that there must be at least two contacts connected to each ring, otherwise, it would be impossible to determine which contacts are the sync contacts.

A method for determining the autocalibration number can use four readings of the autocalibration label 70. Each of the readings is for one set of the contacts 72; the set connected to the inner ring 74, the set connected to the outer ring 76, one sync contact, or the other sync contact. After only four readings are taken, it is possible to determine which contact 72 corresponds to which of the four sets. The position of the sync contacts are determined and this is used in conjunction with the reading from the set connected to the inner ring 74 to determine the autocalibration number. The contacts 72 connected to the inner ring 74 are considered logical zeroes, and the contacts 72 connected to the outer ring 74 are considered logical ones.

A selected predefined calibration encoded pattern consists of the conductive pads 72 interconnected by the conductive inner and outer rings 74 and 76. Calibration data is encoded using selectively electrically interconnected sets of contacts on the label 70. One or more null contact positions (between contacts A and TI at arrow 80 in FIG. 6B) are isolated from both rings 74 and 76 to serve as a rotary position index. One of the contacts 72 at some known position relative to the sync position 80 represented by contact TO connects to the outer ring 76 so all connections to this contact TO are logical ones. To detect a connection to the inner ring 74 or outer ring 76, at least two connections to that ring are needed to detect continuity. The remaining pads 72 are connected to one or the other rings 74 and 76, the particular connection pattern identifying the calibration code. To minimize label stock, a single pattern advantageously is used with subsequent punching or cutting to isolate selectively each of six pads, positions A through F, from one of the two rings 74 or 76. All contacts 72, positions A through F, TI and TO, except the index or null positions, are connected to one, and only one, of the two rings 74 or 76. A minimum of two pads 72 are connected to each ring 74 and 76. This arrangement facilitates error checking since all of the pads 72 except for the index or sync contact 72 must be accounted for in one of two continuity groups for a reading to be considered valid. A missing label 70 is detected when all contacts appear to be a sync contact; i.e., there are no electrical connections between meter pins 54 because the continuity provided by the label 70 is missing.

In one digital encoding method a series of open and closed circuits representing 0 and 1 are introduced onto a label 70. An autocalibration digital label 70 is encoded by laser cutting or printing to represent a particular calibration code number determined by the connections to the inner ring 74, for example, where A represents 1, B represents 2, C represents 4, D represent 8, D represents 16 and F represents 32. In FIG. 6B, contacts B, C, and F are connected to the inner ring 74 to define the calibration code number.

Figure 11:
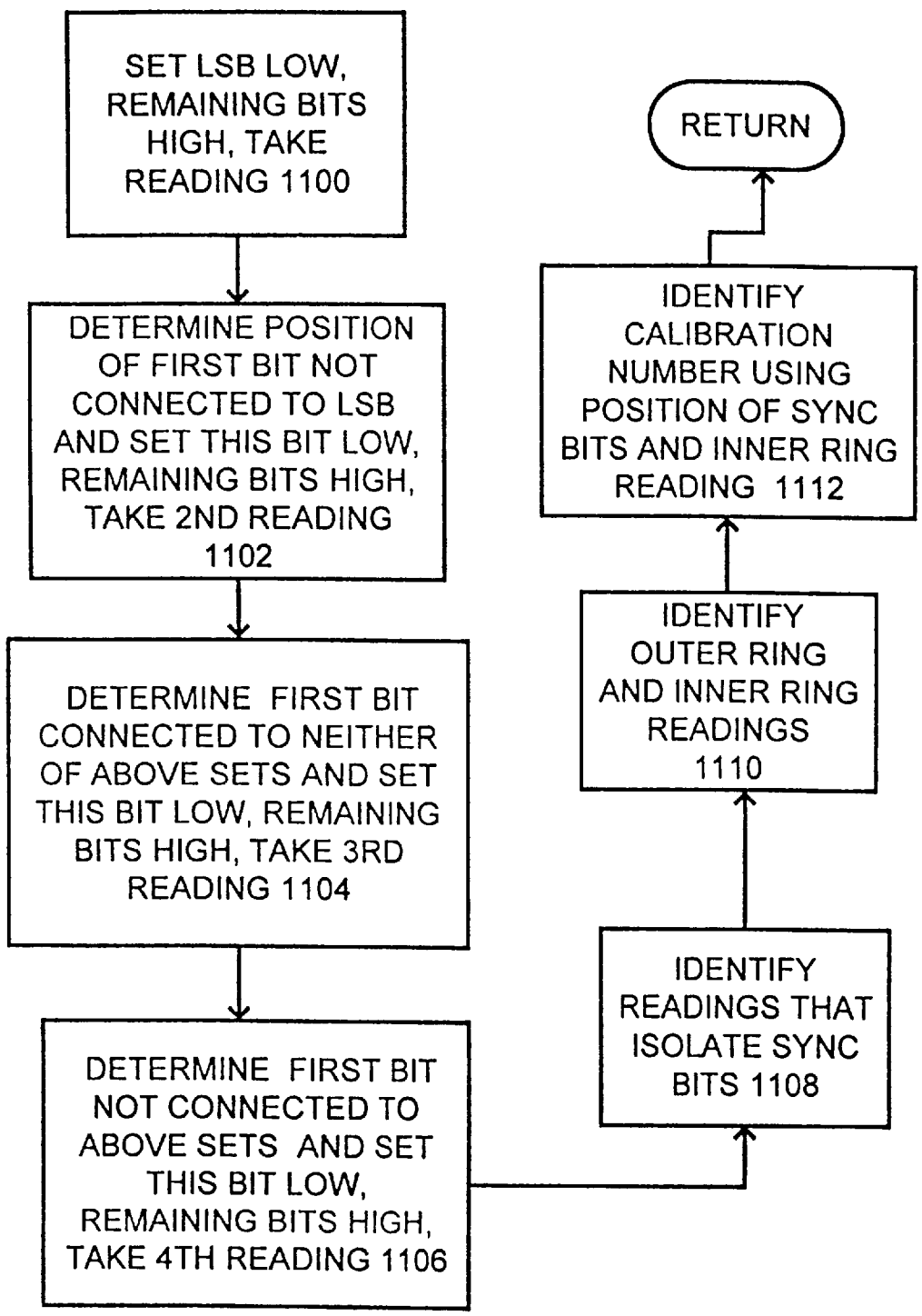

Under software control illustrated and described with respect to FIG. 11, microprocessor 82 configures one contact 72 or bit as a low while the other remaining contacts high. All contacts 72 electrically connected to the particular driven contact 72 are forced low while the remaining contacts are pulled high. By selectively driving contacts 72 and reading the resulting input patterns, the interconnection pattern and associated calibration code is determined. While the unique home or sync position defined by no connection to another contact is used to identify how many sensors 32 remain in the package 50 and to determine the rotary position of the calibration encoded label 70 so that the label contacts 72, A through E, TO and TI can be identified, it should be understood that other configurations can be used with unique patterns of bits to both encode starting position and the calibration code. However, other binary coding schemes provide fewer possible codes for the calibration code number with the same number of label contacts 72.

Alternative calibration encoded labels 70A and 70B for encoding of the calibration information are illustrated in FIGS. 6C and 6D, respectively. In any label 70, 70A and 70B, the actual physical locations of the contacts relative to each other is not important for decoding the label 70 as long as they are in known or predefined positions.

Referring to FIGS. 6C and 6D, ten label contacts 72 are represented by contact A through contact J. As in FIG. 6B, there are three groupings or sets of contact connections including null or SYNC, outer ring 76 or OUTER, and inner ring 74 or INNER. In FIG. 6C for the calibration encoded label 70A with ten contacts A through J, one contact must be the SYNC shown as contact A and one must be tied to the outer ring shown as contact B, and the remaining eight contacts C through J are connected to either the inner ring 74 or the outer ring 76. The eight contacts C through J (codes 0 through 255) represent 256 ($2^8$) possible combinations of connections, minus eight combinations for only one inner ring connection (codes 127, 191, 223, 239, 247, 251, 253, 254), minus one combination for only one outer ring connection (code 0). Calibration encoded label 70A provides 247 unique combinations or codes for the calibration number.

The calibration codes on a particular label 70 can also be used to distinguish between several types of sensors 32. Suppose sensor type "A" required 10 calibration codes, sensor type "B" required 20 calibration codes, and sensor type "C" required 30 calibration codes. The autocalibration codes could be assigned so codes 1 through 10 signify a type "A" sensor with type "A" calibration code 1 through 10, label codes 11 through 30 signify a type "B" sensor with type "B" calibration code 1 through 20, and label codes 31 through 60 signify a type "C" sensor with type "C" calibration code 1 through 30. In this way the label code indicates both the sensor type and calibration code associated with that sensor type.

In FIG. 6D, alternative types 1, 2, 3 and 4 of the calibration encoded labels 70B include two sync positions. In the type 1 calibration encoded label 70B two adjacent sync positions are used which advantageously corresponds to an arrow indicator 80 as shown in FIGS. 4 and 6B to help the user with positioning the label in the sensor meter 10. With the type 1 label 70B, the two adjacent sync contacts are A and B, one contact J is tied to the outer ring 76, and the seven remaining contacts C through I are connected to the inner or outer ring 74 or 76. The seven contacts represent 128 ($2^7$) possible combinations of connections, minus seven combinations for only one inner ring connection, minus one combination for only one outer ring connection. The type 1 calibration encoded label 70B provides 120 unique combinations for the calibration number.

With the type 2, 3 and 4 calibration encoded labels 70B, the relative position of the two sync contacts can be used to provide additional information. Sync contact combinations A and B (no gap) type 1, A and C (gap of 1 space) type 2, A and D (gap of 2 spaces) type 3, and A and E (gap of three spaces) type 4 can be uniquely detected and used to distinguish between four types of calibration encoded labels 70B, each calibration encoded label 70B encoding 120 unique combinations. Sync contact combinations A and F, A and G, A and H, A and I, and A and J are not uniquely distinguishable. Using the four types 1, 2, 3, and 4 of calibration encoded labels 70B provides a total of 480 (4*120) combinations for the calibration number.

Other calibration encoded labels 70 can be provided with the relative position of three or more sync contacts used to generate unique patterns. For example, with three sync contacts and one contact tied to the outer ring, six contacts remain to connect to the outer or inner ring. The six contacts represent 64 ($2^6$) possible combinations of connections, minus seven combinations for only one inner ring connection, minus one combination for only one outer ring connection which leaves 56 unique combinations. There are many ways that the three sync contacts can be uniquely placed: A, B, and C; A, B, and D; A, B, and E; A, B, and F; A, B, and G; A, B, and H; A, B, and I; A, C and E; A, C, and F; etc. As with two sync contacts, these combinations of sync contacts can indicate different types of labels, and for example, to identify one of multiple types of analysis to be performed by the sensor meter 10.

The preferred calibration encoded label arrangement has two rings or paths 74 and 76 as illustrated in FIG. 6B, with contacts connected to one ring, such as ring 74 assigned as logical 0 the other ring 76 as logical 1 for a binary coding method. In another design variation, it is possible to have labels with additional conductors with connections to these conductors assigned as logical 2 (ternary coding), logical 3 (quaternary coding), and the like. This would permit more unique combinations for a given number of label contacts 72.

In FIG. 7A, an analog system generally designated by reference character 150 is shown. Analog system 150 is based on measuring resistance values of resistors 152 (R1 and R2) provided on a label 170, or label 170A of FIG. 7C. The resistance value of resistors 152 (R1 and R2) provides the calibration value. Although it is possible to relate the analog value of the resistance to the calibration value, the preferred arrangement is to print resistors 152 of specific values. For example, to distinguish five calibration codes one of five different resistance values (e.g. 1000Ω, 2000Ω, 3000Ω, 4000Ω, 5000Ω) would be screen printed onto the label 170 or 170A. The resistance values for resistors 152 (R1 and R2) are chosen so the resistance values measured by the processor 82 are easily distinguished from each other even though there may be variations in the resistance due to printing variations or variations in contact resistance where the label 170 or 170A is contacted by the autocalibration pins 54.

In FIG. 7A, VREF is a known reference voltage and resistor 154 RREF is a known reference resistance. An analog-to-digital converter (ADC) 156 converts the analog voltage present at its input labeled VMEAS into a digital value at its output labeled (IA) which is read by the processor 82. A driver 158 (DA) is an analog switch controlled by the processor 82 through a signal line labeled OA. The driver 158 controls a p-channel field-effect transistor (FET) 160 that leaves resistor 154 RREF in the circuit 150 when the driver 158 is turned off or shorts out resistor 154 RREF when the driver 158 is turned on.

The value of resistors 152 (R1 and R2) can be determined as follows. With driver 158 DA turned off, resistor 154 RREF is in the circuit, so resistors 152 (R1 and R2) plus resistor 154 RREF function as a voltage divider. Then the voltage VMEAS is measured and defined as VOFF. With driver 158 DA turned on, RREF is shorted out, so resistors 152 (R1 and R2) function as a voltage divider. Then the voltage VMEAS is again measured and now defined as VON.

The applicable equations are:

$$\text{VOFF} = \frac{R2 + RREF}{R1 + R2 + RREF} \text{ VREF} \qquad [\text{eqn 1}]$$

$$\text{VON} = \frac{R2}{R1 + R2} \text{ VREF} \qquad [\text{eqn 2}]$$

solving eqn 2 for R1:

$$R1 = R2 \frac{\text{VREF} - \text{VON}}{\text{VON}} \qquad [\text{eqn 3}]$$

substituting R1 into eqn 1 and solving for R2:

$$R2 = RREF \frac{\text{VON}(\text{VREF} - \text{VOFF})}{\text{VREF}(\text{VOFF} - \text{VON})} \qquad [\text{eqn 4}]$$

REF and RREF are known values and VOFF and VON are measured values. In eqn 3 the values for R2, VREF, and VON are substituted to calculate R1. At this point R1 and R2 are known so the calibration value can be determined.

To distinguish many calibration codes, more than one resistor could be used. For a label 70 with m resistors where each resistor may be any of n values, then the number of calibration codes is $m^n$.

For example, printing two resistors 152 (R1 and R2) where each resistor 150 could have one of five distinct resistance values permits 25 (i.e. 5*5 or $5^2$) calibration codes to be distinguished. This can be expanded to three resistors 152 could provide 125 (i.e. 5*5*5 or $5^3$) calibration codes, and so on.

Having reference to FIG. 7B, an analog two resistor label 170 is illustrated. An inner resistance 152 (R2) and outer resistance 152 (R1) can be replicated ten times (once for each rotary position of the sensor package 50) while only three autocalibration pins 54 are needed, as shown in FIG. 7A. The autocalibration pins 54 are placed in a line. One pin 54 (PA) would contact the contact pad at the common junction (I) of all the inner resistors 152 (R2). Another pin 54 (PB) contacts a junction (J) of the inner resistor R2 and the outer resistor 152 R1. The third pin 54 (PC) contacts the other end (O) of the outer resistor 152 (R1).

A variation of the label 170 of FIG. 7B can have only one inner resistor 152 (R2) and one outer resistor 152 (R1), with continuous conductive rings to make contact with the autocalibration pins 54. One ring (not shown) would be at the diameter of the junction (J) of resistors 152 (R1 and R2). The other ring (not shown) would be located at the diameter of the other end (O) of resistor 152 R1. The conductive rings would be made of low resistance material. The meter autocalibration pins 54 would contact the center contact (I) and the two rings, as with the label 170.

Another style of two resistor label 170A is illustrated in FIG. 7C. The three autocalibration pins 54 are placed in a line. One pin 54 (PB) would contact the junction 176 of all ten resistors 152. Another pin (PA) would connect to the end 174 of resistor R1. The third pin (PC) would be in a line with the other two pins and connect to the end 174 of resistor R2. If the set of resistance values for resistance R1 (e.g. n1 values) were different than the set of resistance values for resistance R2 (e.g. n2 values) then n1*n2 different calibration codes could be distinguished.

For the FIG. 7C style label 170A, where values of the two resistors 152 are chosen from the same set of n resistances then some combinations are not distinguishable because the label rotates, e.g. R1=1000Ω and R2=2000Ω can not be distinguished from R1=2000Ω and R2=1000Ω. The number of different combinations of two resistors of the style of Figure B where each resistor may be one of n values is given by the equation:

$$\frac{n(n-1)}{2} + n.$$

Having reference to FIG. 7D, the number of different resistance values and the number of distinct calibration codes than can be determined is tabulated.

Figure 8:
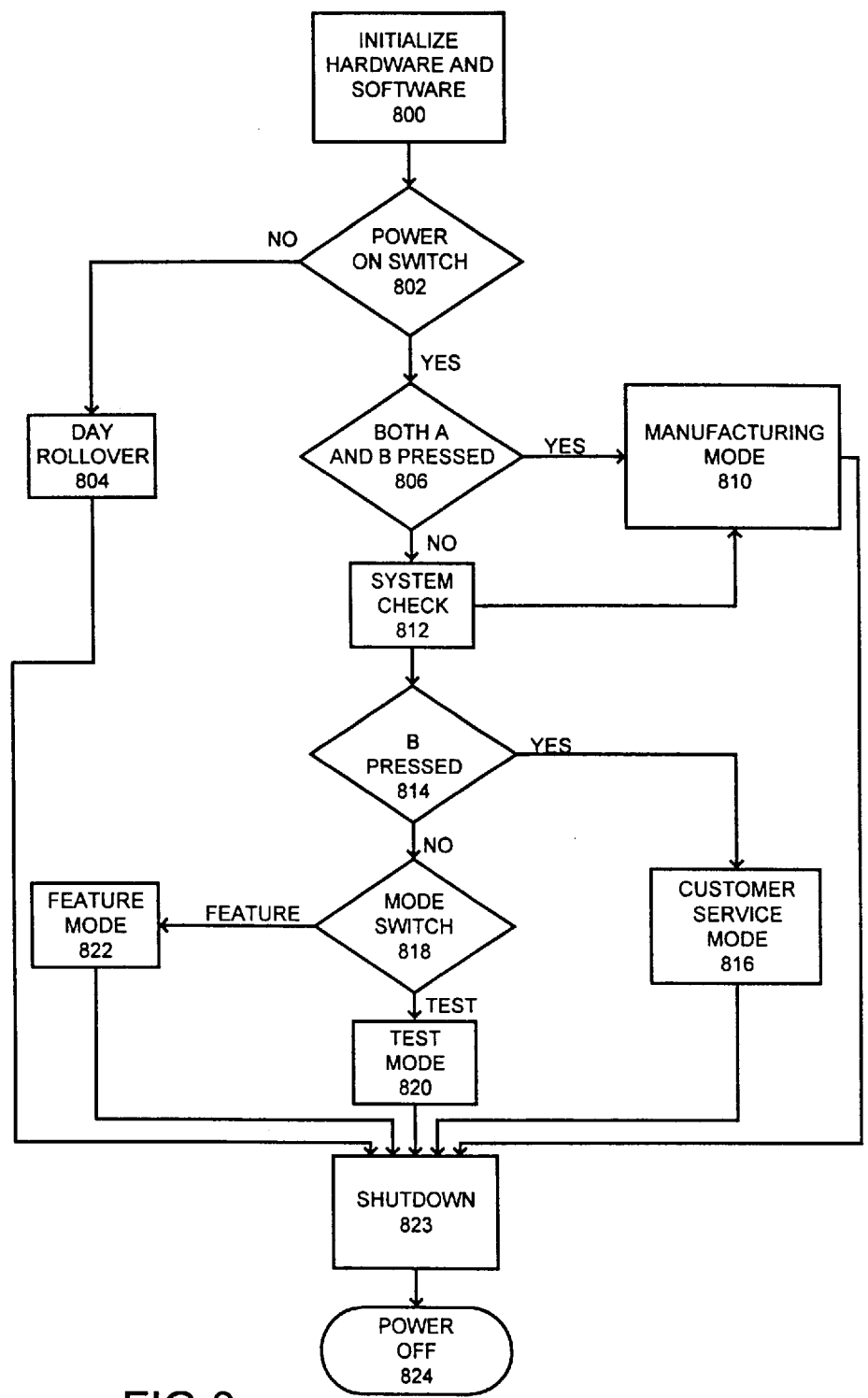
FIGS. 8, 9, 10, and 11 are flow charts illustrating logical steps performed in accordance with the present invention of the autocalibration encoding method by the sensor meter of FIG. 1.

Referring to FIG. 8, sequential steps performed by microprocessor 82 begin at a block 800 with initializing the hardware and software of sensor meter 10. An ON input at line 28A (FIG. 5) is identified as indicated at a decision block 802. Microprocessor 82 processes a day rollover as indicated at a block 804. When the ON input is identified at block 802, checking for both A(44) and B(42) buttons pressed is provided as indicated at a decision block 806. When both A(44) and B(42) have been pressed, a manufacturing mode is processed as indicated at a block 810. Otherwise, a system check is performed as indicated at a block 812. Then checking for B(42) pressed is provided as indicated at a decision block 814. If B(42) has been pressed, then a customer service mode is processed as indicated at a block 816. Otherwise, the mode switch is checked as indicated at a decision block 818. When the test selection is identified at block 818, then the test mode is processed as indicated at a block 820. When the feature selection is identified at block 818, then the feature mode is processed as indicated at a block 822. Microprocessor 82 processes sensor shutdown as indicated at a block 823 and poweroff as indicated at a block 824.

Figure 9:
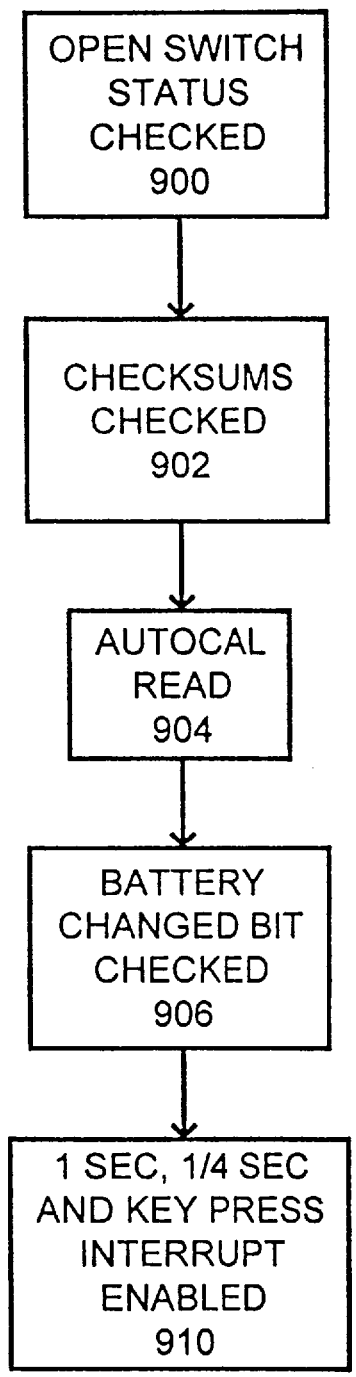

Referring to FIG. 9, sequential steps performed by microprocessor 82 for system checking begin with checking for an open switch status as indicated at a block 900. Microprocessor 82 checks the integrity of memory 54 as indicated at a block 902. Microprocessor 82 checks the calibration encoded label 70 in accordance with the invention as indicated at a block 904. Exemplary steps performed for reading and decoding the calibration encoded label 70 are further illustrated and described with respect to FIG. 10. Microprocessor 82 checks a battery changed bit to identify a low or dead battery as indicated at a block 906. Microprocessor 82 enables 1 second, ¼ second, and key press interrupt as indicated at a block 910.

Figure 10:
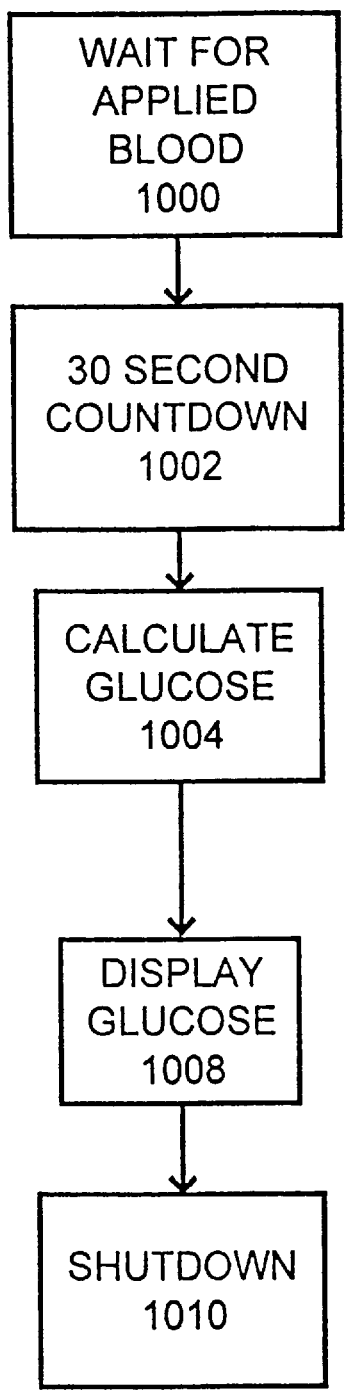

Referring to FIG. 10, sequential steps performed by microprocessor 82 for the test mode begin with waiting for an applied blood sample as indicated at a block 1000. When the user applies a blood sample to the sensor 32 that is identified at block 1000, then the microprocessor 82 starts a 30 second countdown as indicated at a block 1002. A glucose value is calculated by the microprocessor 82 using the calibration code value read at block 904 in FIG. 9, as indicated at a block 1004. The glucose value is displayed for viewing by the user as indicated at a block 1008. Microprocessor 82 processes shutdown as indicated at a block 1010.

Referring to FIG. 11, sequential steps performed by microprocessor 82 for decoding the calibration encoded label 70 are shown. The sequential operations begin with microprocessor 82 setting the least significant bit (LSB) low, the remaining bits high, and taking a reading as indicated at a block 1100. Microprocessor 82 determines from the first reading the position of the first bit in the label 70 that is not connected to the least significant bit, and this bit is set low, the remaining bits high, and a second reading is taken as indicated at a block 1102. This bit set low before the second reading is the first, or least significant bit that is a 1. Microprocessor 82 determines the first bit that was connected to neither of the above sets which is the least significant bit that is a 1 in both readings, sets this bit low, the remaining bits high, and takes the third reading as indicated at a block 1104. Microprocessor 82 determines the first bit that was connected to none of the above sets which is the least significant bit that is a 1 in previous three readings, sets the identified bit low, the remaining bits high, and takes the fourth reading as indicated at a block 1106. Microprocessor 82 determines which of the four readings isolates the sync contacts where the readings have only one zero bit as indicated at a block 1108. Microprocessor 82 determines which of the remaining two readings is from the outer ring 76 and which one is from the inner ring 74 as indicated at a block 1110. Identifying the inner and outer rings 74 and 76 is done using the position of the sync bits identified at block 1108, and the known fixed pattern of the TI and TO contacts. Microprocessor 82 uses the position of the sync bits and the reading of the inner ring to determine the autocalibration number as indicated at a block 812. For example, the bits defining the autocalibration number can include bits FEDCBA.

In the four readings, no bit can be present, or connected, for more than one reading. In other words, a bit can be a zero in only one of the four sets. The zeroes in all four sets are mutually exclusive. Two of the four readings must be for the sync positions. That is, two of the readings must have only one zero and these must be in adjacent positions. The pattern of the TO and TI bits must exist exactly. That is, all connections to contact TO are assigned logical 1, connections to contact TI are assigned logical 0 and contacts TO and TI can not be connected together. Microprocessor 82 looks for this exact circumstance, based on the position of the sync contacts. The autocalibration number identified at block 812 must be between 1 and 62, inclusive.

A digitally implemented calibration encoded label 70, 70A or 70B has several advantages. First, with the sensor package 50 rotated within the sensor meter 10 to any or multiple rotary positions with the digitally encoded calibration encoded label 70, 70A or 70B including at least one allocated position to define a home, i.e., the contact pad position without any connections to either ring 74 or ring 76, the software for deciphering the calibration code is simplified. Second, the inner and outer rings 74 and 76 with connecting traces provide a means of determining if the instrument has made contact to the calibration encoded label properly. The digitally encoded autocalibration label 70, 70A or 70B can be encoded by cutting either trace at those position that have both traces. Sensing of those positions connected along the inner ring 74 provides calibration information, while sensing of the remaining positions verifies that the contact pins have made contact to those positions properly. It is believed that most common failure mode will be improper contact to the label or an open circuit. An error is also detectable when neither trace is cut. Third, a digital system is more robust with respect to signal detection. In an analog or resistive version, careful control of the print thickness, the inks and the contact resistance are necessary to differentiate different calibration levels. While these parameters are still important for a digital system, the requirements can be relaxed without compromising the information contained in the label. Fourth, the process for producing the digital calibration encoded label 70 is simplified to a single printing step and subsequent marking. An analog version of calibration encoded label 70 requires multiple print steps with different inks to produce a complete label. Fifth, the number of possible calibration lines can approach 256 or $2^8$. This number of calibration lines provides excess capacity and flexibility that could not be obtained easily with an analog system. Also, extra positions, such as, TI and T2, in FIG. 6A can be used to increase the number of calibration lines beyond 64 or could be used to designate different products, such as, a test sensor 32 for testing a particular parameter other than glucose. Finally, the use of a single label which is marked to encode information reduced processing costs and inventory requirements. Processing costs are reduced because a single ink is required for label printing. Several conductive inks, each with a different resistivity, are required in the analog scheme. Inventory costs are minimized because the same label is produced each time. When the calibration level has been determined, the digital calibration encoded labels 70 are marked by cutting the appropriate traces. It should be understood that the digital calibration encoded labels 70 can be encoded by printing labels without the appropriate traces to the inner ring 74 or outer ring 76.

While the present invention has been described with reference to the details of the embodiments of the invention shown in the drawings, these details are not intended to limit the scope of the invention as claimed in the appended claims.

What is claimed is:

1. A system for determination of analyte concentration in a test sample comprising:

sensor means for receiving a user sample;

processor means responsive to said sensor means for performing a predefined test sequence for measuring a predefined parameter value; and autocalibration code means coupled to said processor means for providing autocalibration encoded information read by the processor, said autocalibration encoded information being utilized by the processor for said predefined test sequence; said autocalibration code means comprising a plurality of electrical contacts defining said autocalibration encoded information; and wherein said plurality of electrical contacts defining said autocalibration encoded information include at least two connected contacts defining a sync position.

2. A system as recited in claim 1 wherein said plurality of electrical contacts include a predefined encoded bit pattern defining a calibration code.

3. A system as recited in claim 1 wherein said at least two sync contacts being positioned relative to each other for encoding predefined information.

4. A system as recited in claim 3 wherein said at least two sync contacts includes a predefined one of multiple relative position combinations between sync contacts of no gap, a gap of one space, a gap of two spaces, and a gap of three spaces.

5. A system as recited in claim 1 which includes an enclosure, said enclosure formed by a base member and a cover; and said base member supports a predetermined number of autocalibration pins.

6. A system as recited in claim 5 wherein said autocalibration encoded information is defined by electrically interconnected sets of contacts on a label carried by said sensor means; and wherein predefined ones of said autocalibration pins are aligned for electrical contact engagement with predefined contacts on said label.

7. A system as recited in claim 5 wherein said autocalibration encoded information is defined by electrically interconnected sets of contacts printed onto said sensor means, and wherein predefined ones of said autocalibration pins are aligned for electrical contact engagement with predefined contacts printed on said sensor means.

8. A system as recited in claim 1 wherein said autocalibration encoded information is defined by electrically interconnected sets of contacts on a label carried by said sensor means; said interconnected sets of contacts including multiple contacts representing a logical one; multiple contacts representing a logical zero; and at least one null contact.

9. A system as recited in claim 8 wherein said at least one null contact identifies a home position for a package containing multiple sensor means.

10. A system as recited in claim 1 wherein said autocalibration code means is formed by electrically conductive material providing an analog resistance value defining said autocalibration encoded information.

11. A system as recited in claim 10 further includes analog circuitry for coupling said autocalibration code means to said processor means.

12. A system as recited in claim 1 wherein said autocalibration code means is formed by electrically conductive material providing a digital encoded value defining said autocalibration encoded information.

13. A system as recited in claim 12 further includes digital circuitry for coupling said autocalibration code means to said processor means.

14. A system as recited in claim 1 in which the sensor means receives a body fluid as the user sample and the concentration of a preselected analyte in the body fluid is the predefined parameter value.

15. A system as recited in claim 14 in which the body fluid is blood and the analyte is glucose.

16. A system as recited in claim 1 which is responsive to the user sample by detecting a change in conductivity therein.

17. A system as recited in claim 1 which is responsive to the user sample by detecting a change in conductivity therein.

18. The system of claim 1 which is a sensor by virtue of the sensor means employing an enzymatic reaction for performing said predefined test sequence.

19. A method for calibrating a sensor comprising the steps of:

providing the sensor system with a sensor for receiving a user sample and a processor for performing a predefined test sequence for measuring a predefined parameter value;

providing calibration encoded information with said sensor, reading said calibration encoded information by said processor and utilizing said calibration encoded information for said predefined test sequence;

wherein said step of providing calibration encoded information with said sensor includes the step of defining a calibration encoded label on a package containing multiple sensors; and wherein said step of defining said calibration encoded label on said package containing multiple sensors includes the steps of providing multiple contacts on said package; connecting selected different ones of said multiple contacts to define a first set and a second set of connected contacts; said first set of connected contacts representing a logical one and said second set of connected contacts representing a logical zero; and providing at least one null contact of said multiple contacts; said null contact not connected to said first set and said second set of connected contacts.

20. A method for calibrating a sensor as recited in claim 19 wherein said step of reading said calibration encoded information by said processor includes the steps of applying a signal to said multiple contacts, reading a resulting signal pattern; and decoding said calibration encoded information.

21. A method for calibrating a sensor comprising the steps of:

providing the sensor system with a sensor for receiving a user sample and a processor for performing a predefined test sequence for measuring a predefined parameter value;

providing calibration encoded information with said sensor, reading said calibration encoded information by said processor and utilizing said calibration encoded information for said predefined test sequence; and wherein said step of providing calibration encoded information with said sensor includes the step of providing multiple electrical contacts on a package containing said sensor; selectively connecting together different ones of said multiple contacts to define said calibration encoded information; and providing at least one null contact of said multiple contacts; said null contact not connected to another of said selectively connected together different ones of said multiple contacts; and wherein said step of step of reading said calibration encoded information by said processor includes the steps of applying a signal to said multiple contacts, reading a resulting signal pattern; and decoding said calibration encoded information.

\* \* \* \* \*